(12) United States Patent
Oprandi

(10) Patent No.: US 8,221,367 B2
(45) Date of Patent: Jul. 17, 2012

(54) DISPOSABLE URINE CONTROL DEVICE

(76) Inventor: Arthur V. Oprandi, Osprey, FL (US)

( * ) Notice: Subject to any disclaimer, the term of this patent is extended or adjusted under 35 U.S.C. 154(b) by 949 days.

(21) Appl. No.: 11/804,910

(22) Filed: May 21, 2007

(65) Prior Publication Data

US 2007/0260205 A1 Nov. 8, 2007

Related U.S. Application Data

(63) Continuation-in-part of application No. 11/030,630, filed on Jan. 6, 2005, now abandoned.

(51) Int. Cl.
*A61F 5/44* (2006.01)
(52) U.S. Cl. ......................... 604/329; 4/144.4
(58) Field of Classification Search .................. 604/329, 604/327, 385.01, 385.02; 600/574; 4/144.1–144.4
See application file for complete search history.

(56) References Cited

U.S. PATENT DOCUMENTS

| | | |
|---|---|---|
| 1,407,872 A | 2/1922 | Lacy |
| 1,510,973 A | 10/1924 | Behan |
| 2,878,486 A | 3/1959 | Bartlett et al. |
| 3,613,122 A | 10/1971 | Gross et al. |
| 3,964,111 A | 6/1976 | Packer |
| 4,023,216 A * | 5/1977 | Li ................. 4/144.3 |
| 4,206,249 A | 6/1980 | Suzuki et al. |
| 4,296,502 A | 10/1981 | Bortle |
| 4,496,355 A | 1/1985 | Hall et al. |
| 4,531,245 A | 7/1985 | Lowd et al. |
| 4,568,339 A * | 2/1986 | Steer ................. 604/329 |
| 4,681,573 A | 7/1987 | McGovern |
| 4,751,751 A | 6/1988 | Reno |
| 4,756,029 A * | 7/1988 | Zieve et al. ............. 4/144.4 |
| 4,771,484 A | 9/1988 | Mozell |
| 4,815,151 A | 3/1989 | Ball |
| 4,857,064 A | 8/1989 | Mendoza |
| 4,936,838 A * | 6/1990 | Cross et al. .............. 604/329 |
| 4,937,890 A | 7/1990 | Tafur |
| D310,124 S | 8/1990 | Knowles |
| 5,091,998 A | 3/1992 | Witzke |
| 5,243,712 A | 9/1993 | Cross |
| 5,295,983 A * | 3/1994 | Kubo ..................... 604/329 |
| 5,330,453 A | 7/1994 | Cornellier |
| 5,333,330 A | 8/1994 | Murtagh |
| 5,370,637 A | 12/1994 | Brodeur |
| 5,401,263 A | 3/1995 | Cornellier |
| 5,408,703 A | 4/1995 | Cicio |
| D379,225 S | 5/1997 | Canahuate et al. |
| 5,687,429 A | 11/1997 | Rahiff |

(Continued)

*Primary Examiner* — Tatyana Zalukaeva
*Assistant Examiner* — Benedict L Hanrahan
(74) *Attorney, Agent, or Firm* — Charles J. Prescott

(57) ABSTRACT

A disposable urine control device for females during urination when in a crouched position. The control device is provided preferably folded flat and preferably packaged in a stack, each including an elongated flexible folded panel formed of disposable material and having side margins preferably narrowing toward a central portion from enlarged end portions thereof. A perimeter sealing bead extends upwardly from, and substantially continuously around the panel perimeter to provide stiffness and sealing against the labia majora of a female to contain urine within the perimeter sealing bead during urination. A flexible elongated conduit is connected at one end thereof in alignment with a urine drainage aperture formed into a central portion of the panel. When the panel and conduit are unfolded for use from a substantially flat folded orientation of the panel and a folded orientation of the conduit, urine is directed through the conduit into a toilet bowl. An inner sealing bead and urine impermeable layers may also be provided.

6 Claims, 10 Drawing Sheets

U.S. PATENT DOCUMENTS

| | | |
|---|---|---|
| 5,742,948 A | 4/1998 | Cicio |
| 5,893,176 A | 4/1999 | Magiera et al. |
| 5,966,748 A | 10/1999 | Young et al. |
| 5,991,932 A | 11/1999 | Wagner |
| 6,123,691 A | 9/2000 | Karavani et al. |
| 6,154,891 A | 12/2000 | Wilson |
| 6,202,225 B1 | 3/2001 | Beck et al. |
| 6,327,716 B1 | 12/2001 | Kaus |
| 6,434,757 B1 | 8/2002 | Filsouf |
| 6,460,200 B1 | 10/2002 | Mottale et al. |
| 6,475,198 B1 | 11/2002 | Lipman et al. |
| 6,505,355 B1 | 1/2003 | Mutke |
| 6,547,771 B2 | 4/2003 | Robertson et al. |
| 6,716,181 B2 | 4/2004 | Spencer et al. |
| 6,719,741 B2 | 4/2004 | Ching |
| 6,814,719 B2 | 11/2004 | Preston et al. |

* cited by examiner

DISPOSABLE URINE CONTROL DEVICE

CROSS-REFERENCE TO RELATED APPLICATIONS

This application is a continuation-in-part of application of application Ser. No. 11/030,630 filed on Jan. 6, 2005.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to devices adapted to facilitate the female urination process while in a standing or crouched position, and more particularly to a disposable urine control device provided in a compact folded easily carryable configuration prior to use.

2. Description of Related Art

Conventionally, females urinate while seated atop an open commode or toilet having an appropriate ring-shaped seat provided for supporting the buttocks area of the female. However, in situations of public use of such facilities, cleanliness is frequently a problem. The use of such public facilities carries with it the risk of infection from an ever-broadening array of bacteria and virus and generally unclean prior usage thereof.

Additionally, in other parts of the world, a seating commode suitable for urination by a female is not even available. Merely a portal into which urine is to be discharged is provided which easily leads to the inadvertent spreading of urine onto skin, clothing and shoes. Moreover, in situations where a female is requested to provide a urine specimen for medical purposes, the inconvenience associated therewith may easily lead to the spreading of urine in inappropriate places.

A number of prior art devices have been patented which disclose structure adapted to facilitate female urination in a controlled fashion. These devices are structured to be manually held in place while in a standing or crouching position and being able to direct urine flow into an appropriate facility or receptacle. These patents are shown herebelow:

| U.S. Pat. No. 1,407,872 | Lacy |
| U.S. Pat. No. 1,510,973 | Behan |
| U.S. Pat. No. 2,878,486 | Bartlett, et al. |
| U.S. Pat. No. 3,613,122 | Gross, et al. |
| U.S. Pat. No. 4,023,216 | Li |
| U.S. Pat. No. 4,296,502 | Bortle |
| U.S. Pat. No. 4,496,355 | Hall, et al. |
| U.S. Pat. No. 4,531,245 | Lowd, et al. |
| U.S. Pat. No. 4,681,573 | McGovern, et al. |
| U.S. Pat. No. 4,756,029 | Zieve, et al. |
| U.S. Pat. No. 4,771,484 | Mozell |
| U.S. Pat. No. 4,937,890 | Tafur |
| U.S. Pat. No. 5,091,998 | Irazabal |
| U.S. Pat. No. 5,333,330 | Murtagh |
| U.S. Pat. No. 5,370,637 | Brodeur |
| U.S. Pat. No. 5,408,703 | Cicio |
| U.S. Pat. No. 5,687,429 | Rahiff |
| U.S. Pat. No. 5,742,948 | Cicio |
| U.S. Pat. No. 5,893,176 | Magiera, et al. |
| U.S. Pat. No. 6,123,691 | Karavani, et al. |
| U.S. Pat. No. 6,154,891 | Wilson |
| U.S. Pat. No. 6,202,225 | Beck, et al. |
| U.S. Pat. No. 6,460,200 | Mottale, et al. |
| U.S. Pat. No. 6,475,198 | Lipman, et al. |
| U.S. Pat. No. 6,505,355 | Mutke |
| U.S. Pat. No. 6,547,771 | Robertson, et al. |
| U.S. Pat. No. 6,716,181 | Spencer, et al. |
| U.S. Pat. No. 6,719,741 | Ching |
| U.S. Pat. No. 6,814,719 | Preston, et al. |
| U.S. Pat. No. D310,124 | Knowles |
| U.S. Pat. No. D379,225 | Canahuate, et al. |

The detractive aspect of reusable devices of this nature, however, is that they are not easily carryable and must be dried or cleaned or rinsed after use so as to prevent odor build-up and inadvertent urine moisture being spread about after use.

To overcome this limitation of cleanliness after use, a number of prior art devices have previously been patented which are directed to single-use disposable urination devices for the female as follows:

| U.S. Pat. No. 4,608,046 | Towfigh |
| U.S. Pat. No. 4,734,941 | DeWitt, et al. |
| U.S. Pat. No. 4,751,751 | Reno |
| U.S. Pat. No. 4,857,064 | Mendoza |
| U.S. Pat. No. 5,243,712 | Cross |
| U.S. Pat. No. 5,330,453 | Cornellier |
| U.S. Pat. No. 5,401,263 | Cornellier |
| U.S. Pat. No. 5,966,748 | Young, et al. |
| U.S. Pat. No. 5,991,932 | Wagner |
| U.S. Pat. No. 6,327,716 | Kaus |
| U.S. Pat. No. 6,434,757 | Filsouf |

Noteworthy as it applies to the present invention, U.S. Pat. No. 4,857,064 teaches a feminine disposable urinating device having both an elongated absorbent layer attached to a longer liquid-impermeable layer and a complex partition structure associated with a flexible tubular conduit having a flange at one end disposed between the partition and the absorbent layer. The urinal cone disclosed in U.S. Pat. No. 6,327,716 is formed from an essentially triangular shape in the collapsed configuration into a funnel-shaped body which is disposable following use. The obvious benefit of the disposable aspect of these prior art patents is the after-urination cleanliness and cleanup which is simply dealt with by the disposal of the device promptly after use.

The present invention also teaches a single-use disposable urine control device which is manually appliable to cover the labia majora area of the female and preferably includes one or two sealing beads which upwardly extend from a pliable, flexible hand-sized panel or layer to insure that urine discharging is contained and either partially absorbed and/or directed to an appropriate facility or receptacle. Additionally, the unique folding features of the invention facilitate packaging one or several of these urine control devices in a compact form ready for one-time use and disposal after use.

BRIEF SUMMARY OF THE INVENTION

This invention is directed to a disposable urine control device for females during urination when in a crouched position. The control device is provided preferably folded flat and preferably packaged in a stack, each including an elongated flexible folded panel or layer formed of disposable preferably liquid-absorbent material and having side margins preferably narrowing toward a central portion from enlarged end portions thereof. A preferred perimeter sealing bead extends upwardly from, and substantially continuously around the panel perimeter to provide stiffness and sealing against the labia majora of a female to contain urine within the perimeter sealing bead during urination. A flexible elongated conduit is connected at one end thereof in alignment with a urine drainage aperture formed into a central portion of the panel. When the panel and conduit are unfolded for use from a substantially flat folded orientation of the panel and an unfolded orientation of the conduit, urine is directed through the conduit into a toilet bowl. An inner sealing bead and urine impermeable layers may also be provided.

It is therefore an object of this invention to provide a disposable urine control device for females which is easily usable and insures control of all urine discharge into an appropriate receptacle or toilet facility.

Still another object of this invention is to provide a urine collecting device for females which is prepackaged in folded configuration for convenient merchandising and use.

Yet another object of this invention is to provide a disposable urine control device having multiple substantially continuous sealing rings for enhanced stiffness during use to insure that no urine flow inadvertently escapes inappropriately.

Yet another object of this invention is to provide a disposable urine control device for females which preferably combines the features of absorbency and liquid impermeability to insure that all discharging urine is either directed into an appropriate facility and/or absorbed for disposal without contaminating the user's hands, skin or clothing.

In accordance with these and other objects which will become apparent hereinafter, the instant invention will now be described with reference to the accompanying drawings.

BRIEF DESCRIPTION OF THE SEVERAL VIEWS OF THE DRAWING(S)

DETAILED DESCRIPTION OF THE INVENTION

Figure 1:
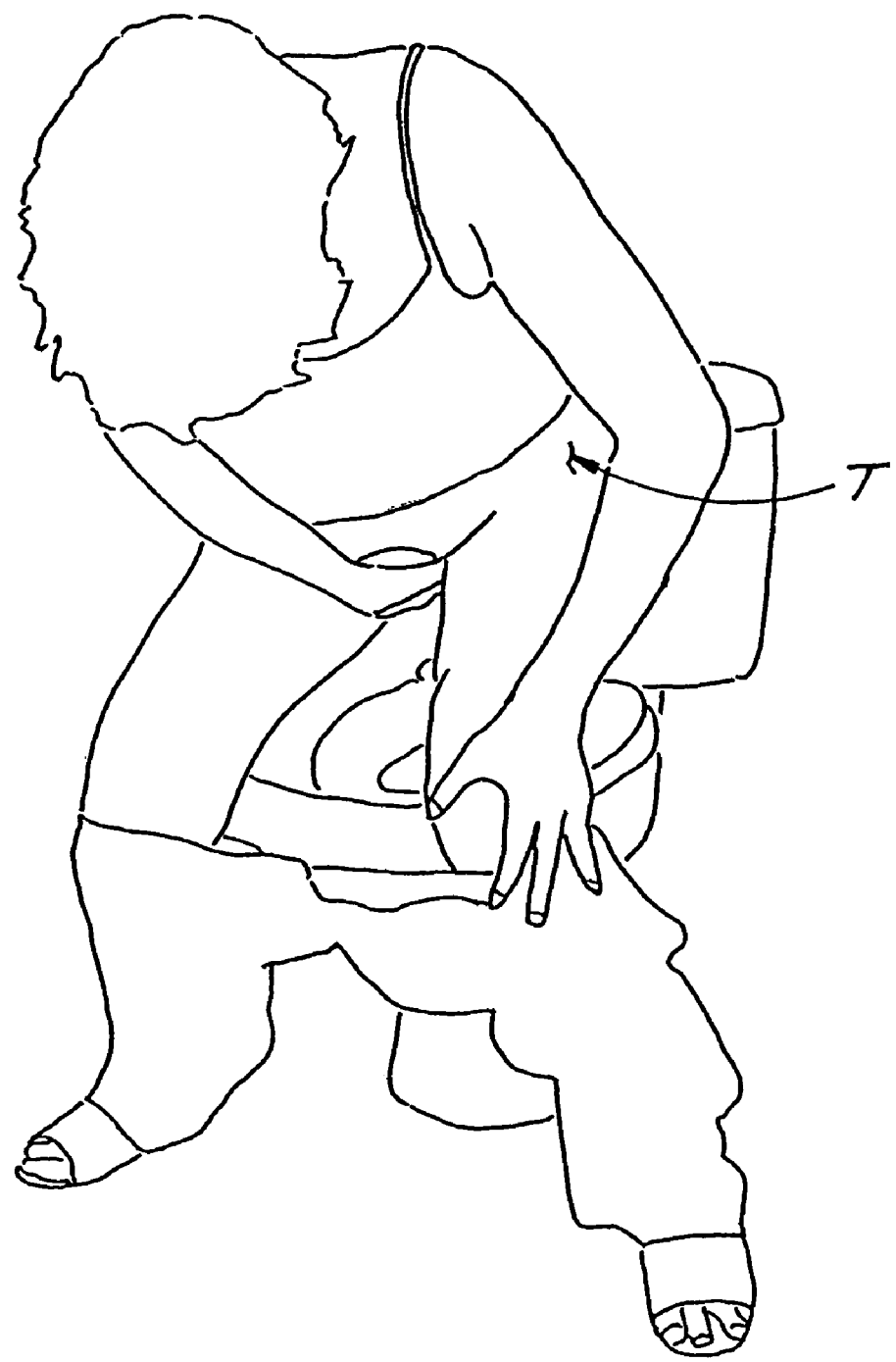
FIG. 1 is a pictorial view of a female in the process of using the preferred embodiment of the invention during urination in a crouched orientation above a toilet facility.
Figure 2:
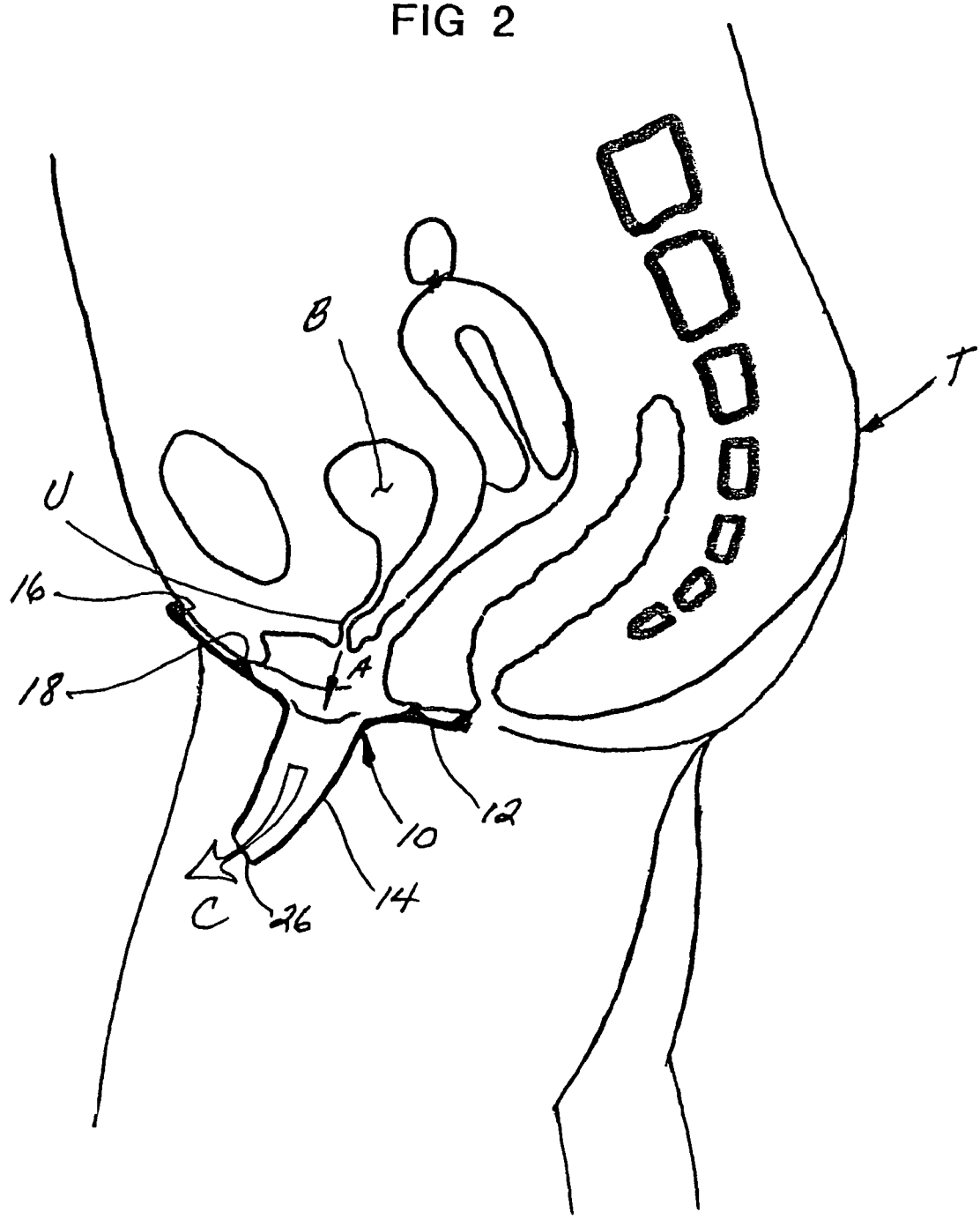
FIG. 2 is a side elevation schematic view of the device hand-held in position for use with respect to the female lower torso anatomy.

Referring now to the drawings, and firstly to FIG. 1, a female is shown in a crouched or partially standing position in the process of urination into a suitable receptacle with the aid of the present invention. The torso T is in a partially angled or crouched orientation to facilitate positioning the device 10 and direction control of urine being deposited into the receptacle. As seen in FIG. 2, the device 10 is in position over the labia majora area in proper alignment to receive urine discharging from the bladder B through the urethra U in the direction of arrow A and finally draining in the direction of arrow C from the elongated conduit 14 as described in detail herebelow.

Figure 3:
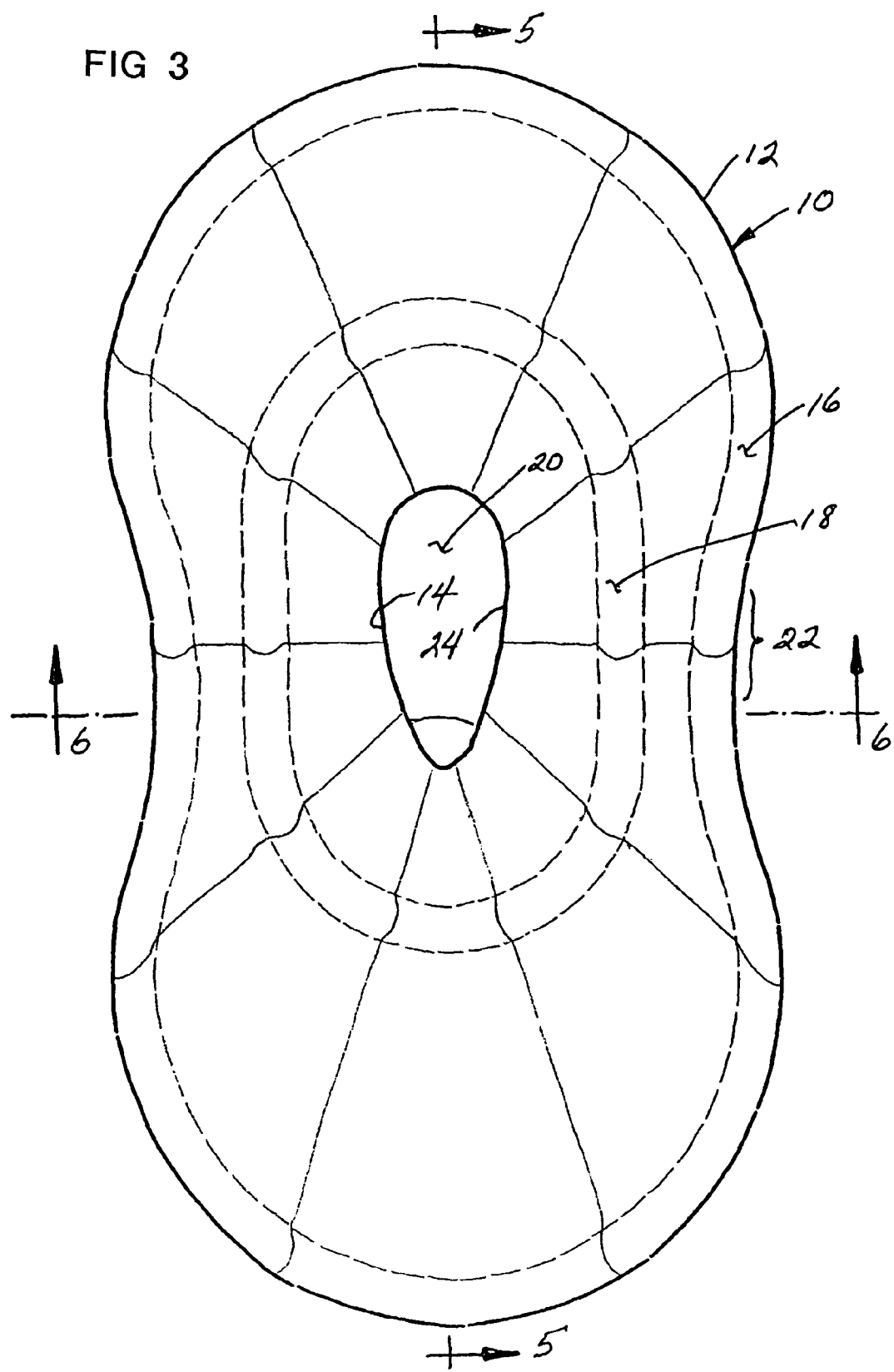
FIG. 3 is a top plan view of the preferred device in the open in-use configuration.
Figure 4:
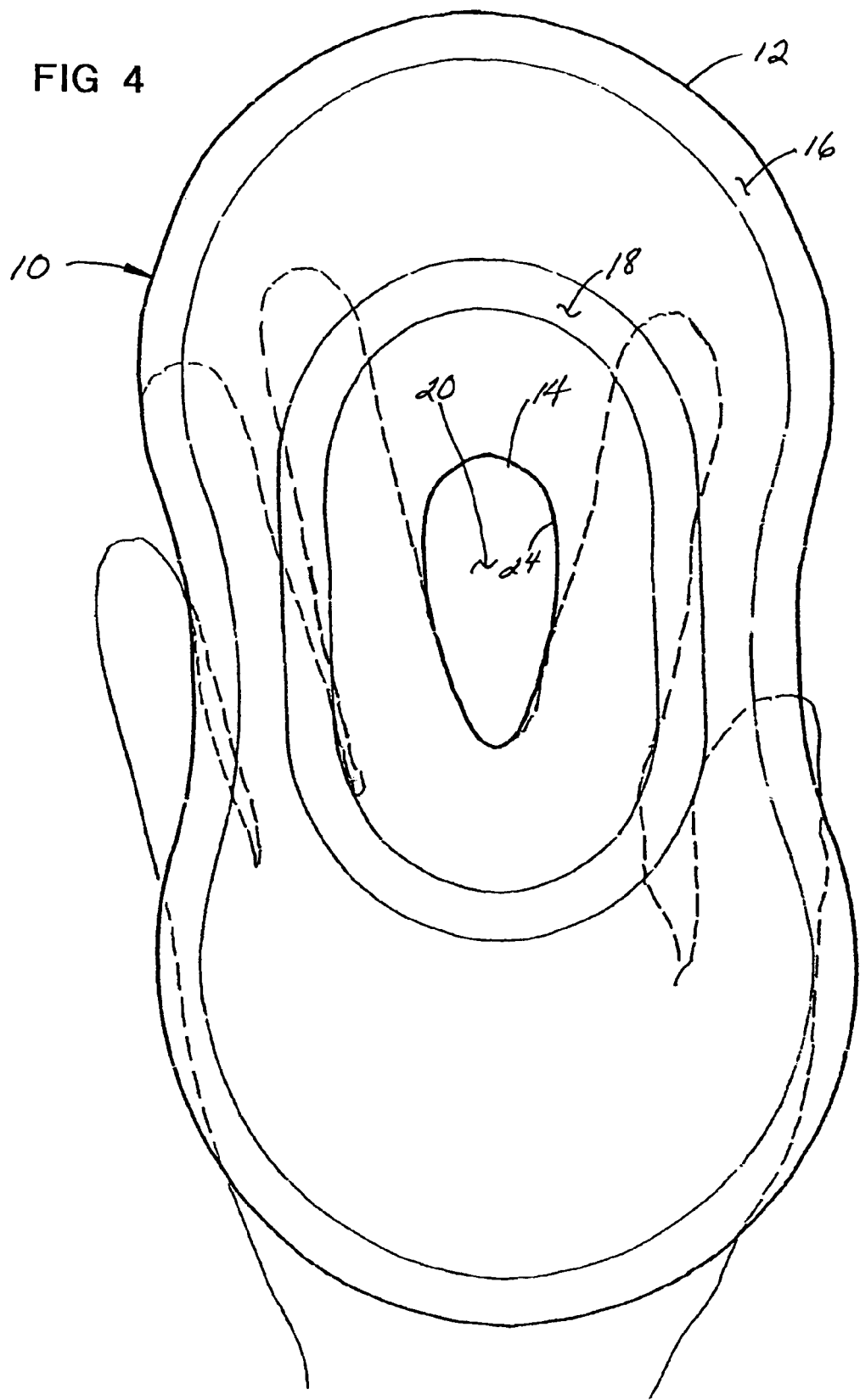
FIG. 4 is a view of FIG. 3 being hand held during use.

As seen in FIGS. 3 to 6, the preferred embodiment of the invention generally shown at numeral 10 includes an elongated pliable or flexible panel or layer 12 which is formed of disposable biodegradable preferably liquid absorbent material and, in the plan view of FIGS. 3 and 4, is configured to be enlarged at each end and arcuately narrowing at 22 toward the central portion of the perimeter margin thereof. The inwardly contoured central perimeter portions 22 facilitate both accurate fore-and-aft and lateral positioning between the legs or thigh areas of the female and preferably cooperate with the perimeter and inner sealing beads 16 and 18 to insure that flowing urine is not splashed inadvertently onto skin, clothing or floor.

Figure 5:
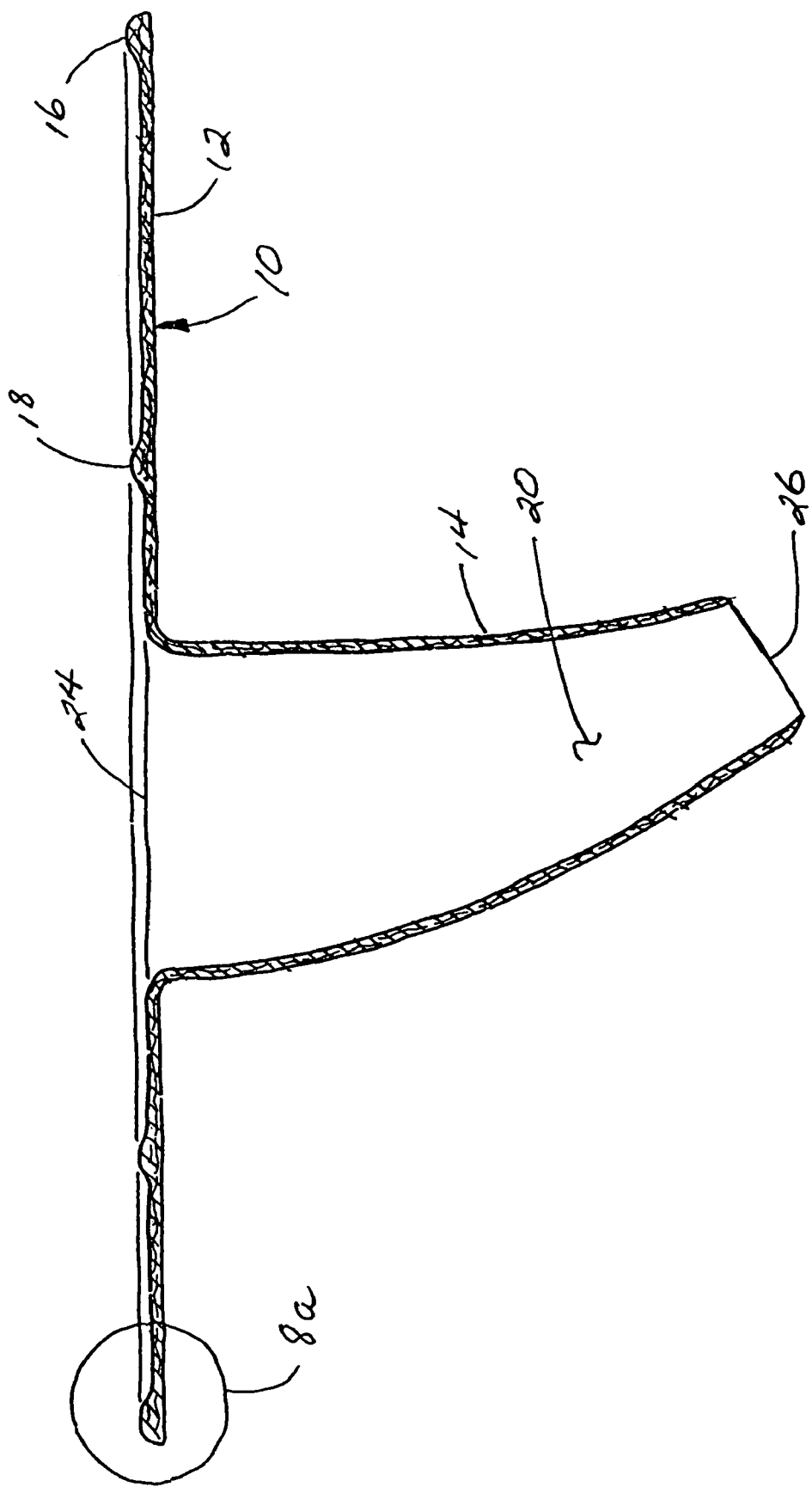
FIG. 5 is a longitudinal section view in the direction of arrows 5-5 of FIG. 3.
Figure 6:
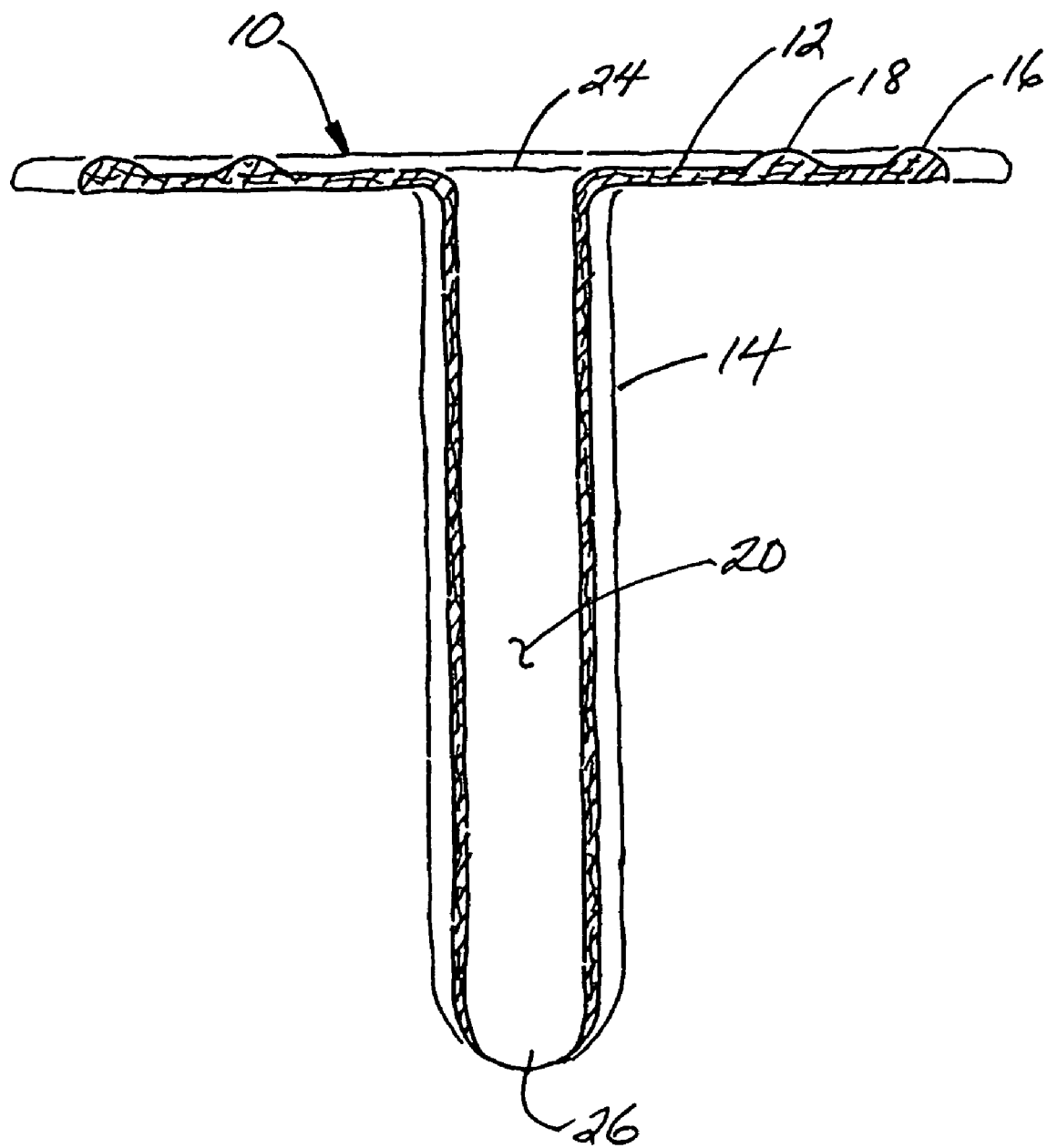
FIG. 6 is a section view in the direction of arrows 6-6 in FIG. 3.
Figure 7A:
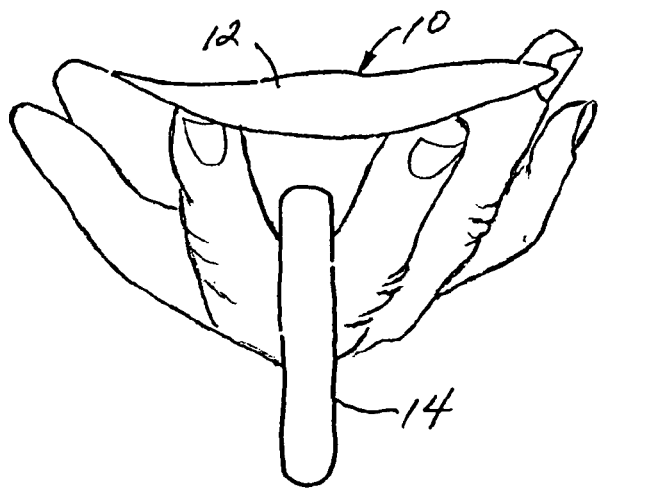
FIGS. 7a to 7d are perspective views showing hand support and manipulation of the preferred device to insure full contact thereof against the labia majora area of the female.
Figure 7B:
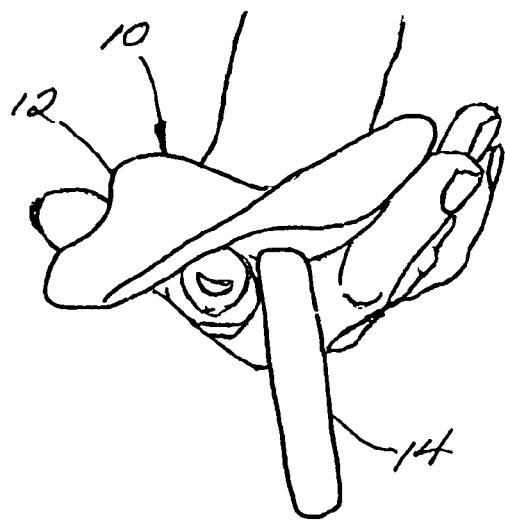
Figure 7C:
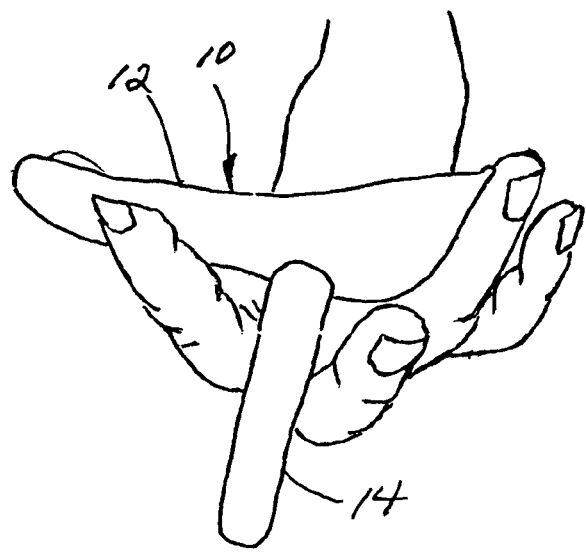
Figure 7D:
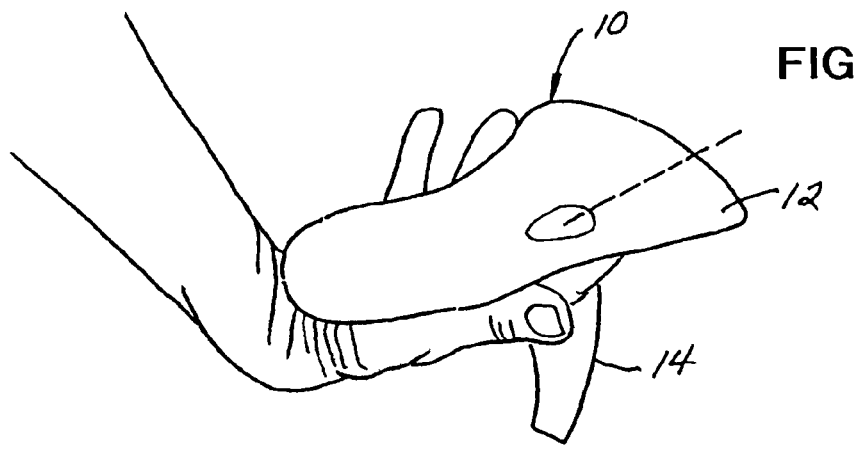

The elongated conduit 14 is integrally or connectedly formed with and extends laterally from an elongated urine drainage aperture 24 as best seen in FIG. 5 to define an elongated hollow passage 20. This conduit 14 is arcuately configured in the side elevation view in FIG. 5 while being substantially straight as shown in FIG. 6 so as to facilitate the direction control of urine discharging therefrom in the direction of arrow C in FIG. 2 from the lower opening 26 thereof.

When in the crouched position, the female has great manual hand control over the positioning and sealing retention of the panel 12 against the labia majora area due to the high flexibility and compliance of the panel 12 as shown in FIGS. 4 and 7a to 7d. This manual flexibility provided by the panel 12 with the conduit 14 positioned between the index and the middle finger of the hand of the user, greatly enhances the accurate placement of the device 10 in position over the labia majora and with the conduit 14 in proper alignment with the urine discharge in the direction of arrow A in FIG. 2.

The perimeter sealing bead 16 extends substantially continuously around the arcuately configured perimeter of panel 12. The configuration of this outer sealing bead 16 is adapted to surround and seal against the perimeter of the labia majora area. The inner sealing bead 18, raised or elevated in the same direction as the perimeter sealing bead 16 and away from the direction of the conduit 14, extends in spaced relationship between the perimeter of the opening or aperture 24 and the perimeter of the panel 12 and is sized to surround and seal against the labia minor area of the female anatomy. The two beads 16 and 18 thus preferably cooperate to add pliant stiffness to the disposable panel 12 while also providing a double seal to prevent urine from inadvertent discharge outwardly between the labia majora and panel 12.

Figure 8F:
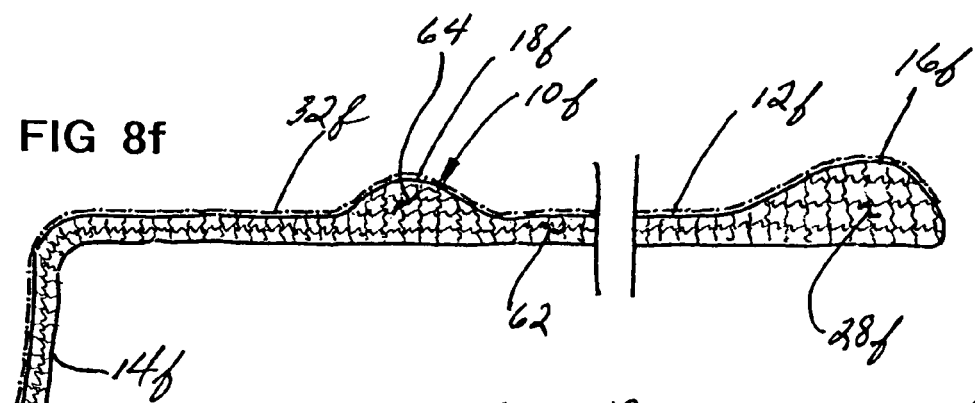
FIGS. 8a to 8h are section views of area 8a of FIG. 5 and alternate embodiments thereof.
Figure 8G:
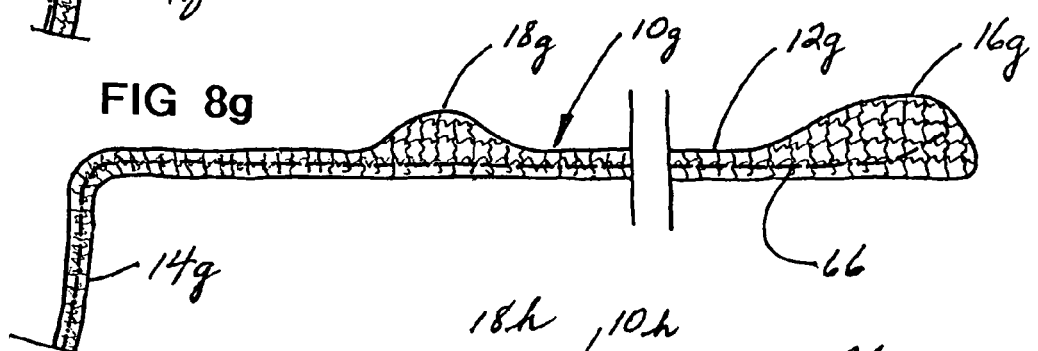
Figure 8H:
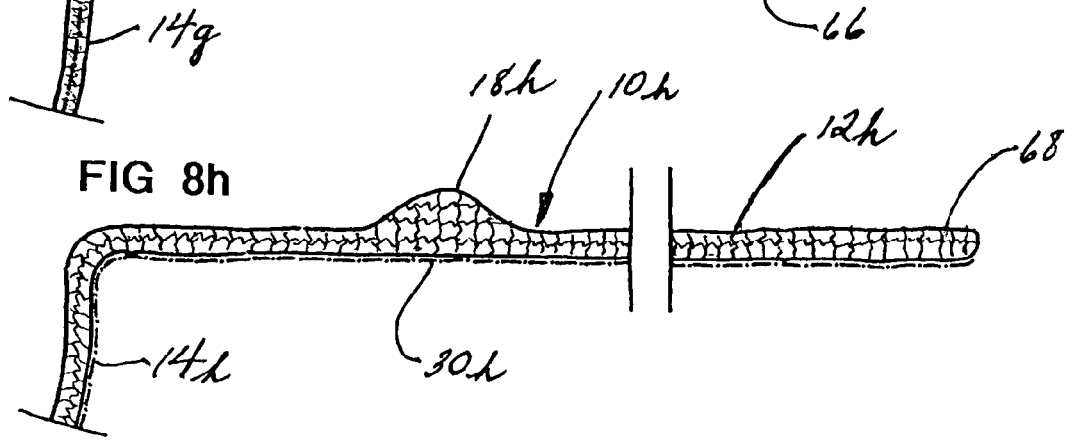
Figure 8A:
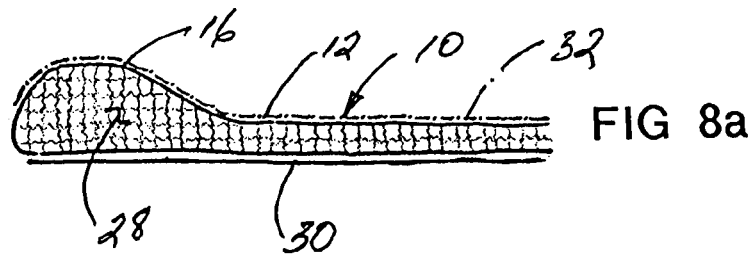

Referring now to FIGS. 8a to 8h, variations of the structure tilized to form the outer sealing bead 16 are there shown. Additionally, variations in the multi-layered structure of the panel 12 itself are also displayed. In FIG. 8a, the layer or panel 12 is formed of fibrous, biodegradable cellulose material of a flexible liquid absorbent nature such that the entire panel 12 is substantially flexible and/or pliantly foldable. Optionally, a thin urine impermeable layer 30 is adhered to the lower surface of the panel 12 so that urine contacting the upper surface will not pass therethrough to make direct contact with the hand holding the device 10 in place during use. Alternately, the urine impermeable layer may be applied as shown in 32 in phantom which provides for hand contact against the softer fibrous surface of the panel 12. In this embodiment 10, the perimeter sealing bead 16 is formed at 28 by providing an enlarged thickened perimeter of homogeneous fibrous absorbent material utilized to form the panel 12 itself.

Figure 8B:
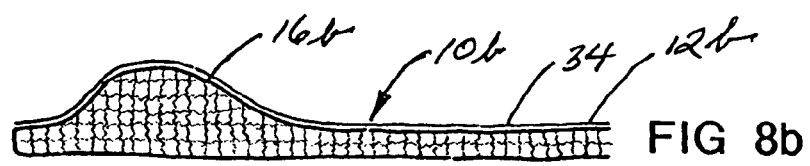
Figure 8C:
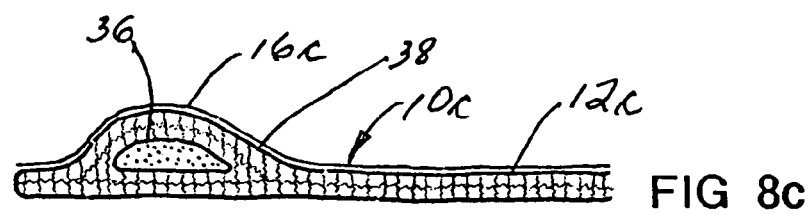

In FIG. 8b, the panel 12b of embodiment 10b is formed, again, of disposable, biodegradable fibrous absorbent cellulose material of a flexible nature. The perimeter sealing bead 16b is formed as an enlarged thickened area immediately adjacent the outer perimeter of the panel 12b. A urine impermeable layer 34 is formed of a biodegradable water impervious or impermeable material well known in the art. In FIG. 8c, the perimeter sealing bead 16c is formed of a fibrous filler material 36 of a more rigid nature which enhances both the useful stiffness of the embodiment 10c and also enhances the urine sealing attributes to further insure that flowing urine passes entirely through the conduit 14 in an appropriate way.

Figure 8D:
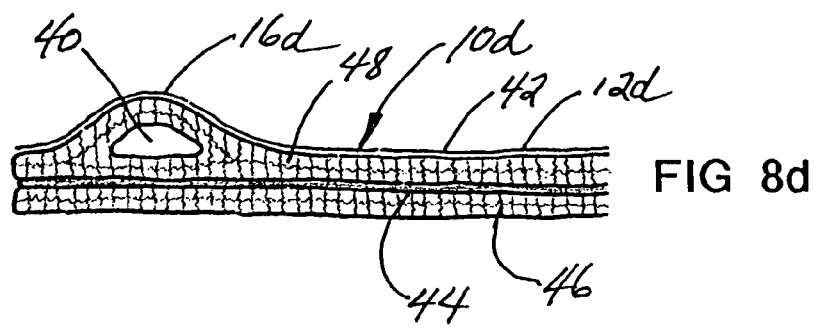

The embodiment 10d in FIG. 8d includes a flexible heat shield layer 44 which is generally coextensive with the entire layer or panel 12d as previously described and is provided so that the hand of the user does not feel the elevated temperature of urine against the upper water impermeable layer 42. Although the disposable, biodegradable fibrous absorbent layers 46 and 48 provide a degree of temperature isolation, the thermal heat shield layer 44 formed of a flexible disposable plastic material greatly reduces heat transfer from the urine to the hand of the user. Additionally, the outer perimeter sealing bead 16d is formed primarily of an air ring or void 40 which is created by the stiffened structure of the thickened fibrous material also defining the outer perimeter bead 16d.

Figure 8E:
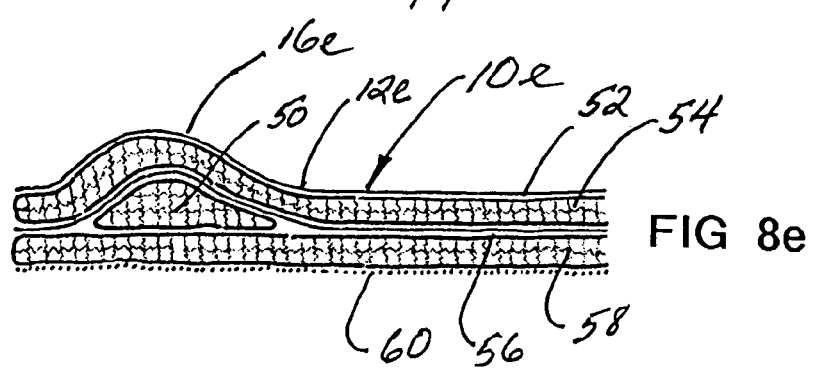

In FIG. 8e, three separate urine impermeable layers or elements are there shown in this embodiment 10e. An upper water impermeable layer 52 is adhered onto an upper fibrous layer 54 as previously described while an intermediate urine impermeable layer 56 is formed between the flexible, absorbent fibrous layers 54 and 58. Additionally, a water-resistant spray is applied at 60 to the lower surface of the panel 12e which does not detract from the soft fibrous feeling of this lower surface of the panel 12e, but does provide for a short term, one-use urine impermeable barrier as triple insurance that all of the urine passes downwardly through the conduit into a suitable receptacle or urine facility or is absorbed.

In FIG. 8f, somewhat similar to the embodiment shown in FIG. 8a, the absorbent, flexible disposable fibrous layer or panel 12f is formed as a single layer having the preferred perimeter sealing bead 16f formed at 28f of an enlarged, thickened perimeter of fibrous, absorbent material similar to that shown at 62 comprising the layer or panel 12f. Similarly, the inner sealing bead 18f is formed of an enlargement or thickening at 64 of this same fibrous disposable material. Optionally, this embodiment 10f may also include a flexible thin water impermeable layer 32f which will substantially prevent any absorbency of the urine discharge causing substantially all of the urine to flow through the conduit 14f.

In FIG. 8g, this embodiment 10g is formed of a layer 12g formed of flexible, absorbent, cellulose or fibrous material having enlargements to define the outer perimeter sealing bead 16g and the inner sealing bead 18g. This embodiment 10g further includes an embedded water impermeable layer 66 which allows a portion of the fibrous material forming layer 12g to absorb some of the urine while preventing the urine from coming in contact with the hand which is pressed against panel 12g.

The embodiment 10h shown in FIG. 8h includes only an inner sealing 12h which, although not preferred, acts in cooperation with the flexibility of the perimeter area 68 of the flexible fibrous layer 12h to help insure that the inner sealing ring 18h accomplishes the intended task of confining all urine discharging during urination and causing it to either be absorbed by the fibrous absorbent layer 12h or be funneled outwardly for proper disposal through the conduit 14h. A water impermeable layer 30h is optionally provided to help insure that, during heavy urination discharge, the absorbency of the fibrous layer or panel 12h is not overtaxed and over saturated.

It should be obvious from the description of the alternate structures of the present invention that at least three separate aspects described therein serve to control and direct the flow of urine into a toilet or suitable container or receptacle. The various placement combinations of water impermeable layers serve to insure that the urine will drain into and flow out from the downwardly extending conduit 14 as previously described. The inner and/or perimeter sealing beads 18 and/or 16, respectively, serve to seal against the labia minora and labia majora areas respectively of the female user to insure urine containment and proper flow and drainage from the conduit. Additionally, in embodiments where urine comes directly in contact with the fibrous biodegradable liquid absorbent material prior to drainage into and through the conduit 14, at least some of the urine will be absorbed and held in this fibrous material primarily as a drip absorbent as the device is removed after urination. Where only water impermeable surfaces come in contact with the urine, there is some slight possibility that dripage after urination and prior to full disposal of the device is prevented.

Figure 9A:
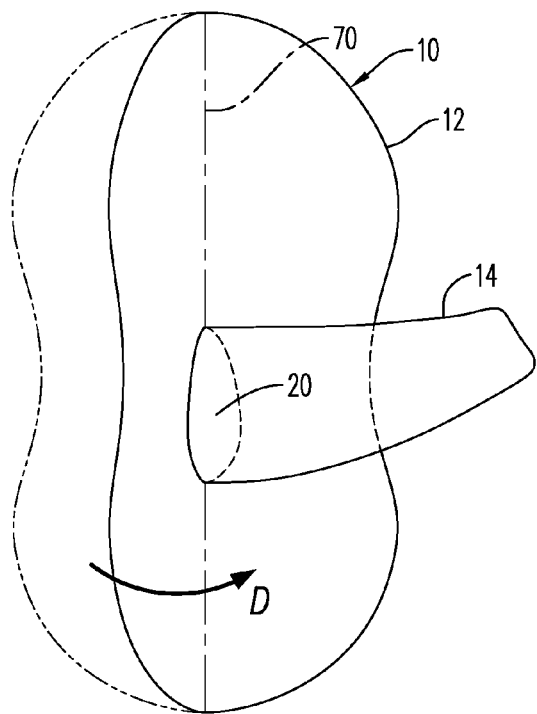
FIGS. 9a through 9d depict the sequence of folding the preferred invention into the folded and stacked arrangement of FIG. 9d.
Figure 9B:
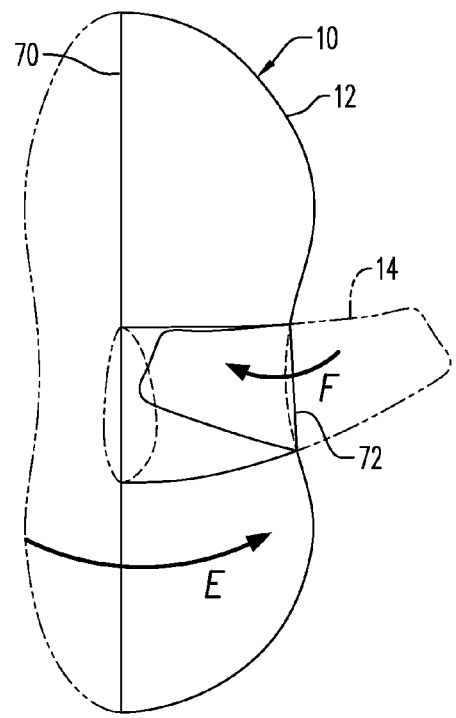
Figure 9C:
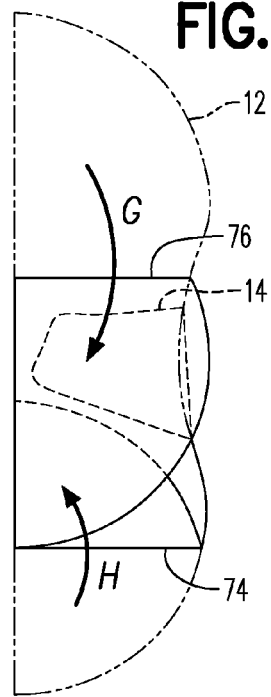

Referring lastly to FIGS. 9a to 9d, the preferred embodiment of the invention 10 is foldable sequentially as there shown. In FIG. 9a, the flexible panel 12 is folded about a longitudinal centerline 70 in the direction of arrow D. In FIG. 9b, the conduit 14 in its flattened orientation is foldable about fold line 72 in the direction of arrow F after the panel 12 is completely folded in half in the direction of arrow E onto its other half along fold line 70. In FIG. 9c, one enlarged end portion of the half folded panel 12 is folded in the direction of arrow G about fold line 76 atop the folded flattened conduit 14, after which the other enlarged end of the half folded panel 12 is folded about fold line 74 thereatop in the direction of arrow H. Thus, the panel 12 is thrice folded while the conduit is twice folded to achieve compactness.

Figure 9D:
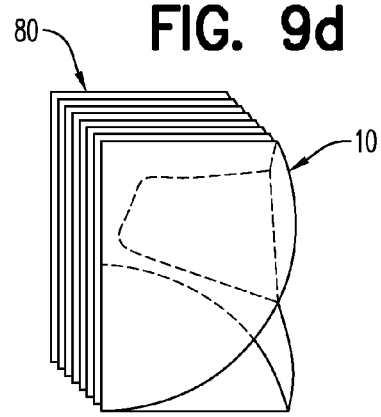

In FIG. 9d, a plurality of the folded ready-to-use devices 10 are shown in a stack 80 which may be bundled or wrapped or containerized in carryable form as desired.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

The invention claimed is:

1. A disposable urine control device for females during urination in a crouched position comprising:
   an elongated flexible folded panel formed of disposable material and having inwardly profiled side margins and enlarged end portions thereof to define a perimeter of said panel;
   a perimeter sealing bead formed as a part of said panel and extending upwardly from, and substantially continuously around said perimeter, said perimeter sealing bead providing stiffness and sealing against the labia majora to contain urine within said perimeter sealing bead during urination;
   a flexible elongated folded conduit formed into a one-piece unit with said panel and being directly connected in alignment with a urine drainage aperture formed into, and laterally extending from, a central portion of said panel into a tubular configuration to convey urine from an open lower end of said conduit;

said panel and said conduit being unfolded for use from a flat folded orientation of said panel and a folded orientation of said conduit;

said panel including two inner urine absorbent layers, a thermal layer disposed between the two absorbent layers, and an outer urine impermeable layer said panel having a longitudinal centerline fold line and two spaced apart transverse fold lines for sequentially folding said panel in half along each respective said fold line to achieve compactness of said device.

2. A disposable urine control device as set forth in claim 1, wherein:

said aperture is generally egg-shaped and elongated lengthwise of said panel to facilitate folding along a longitudinal centerline of said panel and said conduit;

said aperture adapted to fit between two fingers of the hand of a user for accurate alignment of said aperture with urine discharge.

3. A disposable folded urine control device for females during urination in a crouched position comprising:

an elongated flexible flat folded panel formed of disposable material and having narrow side margins and enlarged end portions thereof to define a perimeter of said panel which is compliantly hand-positionable between the legs and covering the labia majora area;

a perimeter sealing bead formed extending upwardly from, and substantially continuously around said perimeter, said perimeter sealing bead providing a seal against the labia majora to substantially contain urine within said perimeter sealing bead;

a separate inner sealing bead formed as a part of said panel and raised upwardly and spaced between said perimeter sealing bead and a urine drainage aperture positioned centrally through said panel, said inner sealing bead establishing sealing contact around the labia minora and cooperating with said perimeter sealing bead to more completely contain urine during urination;

a flexible elongated folded conduit directly connected at one end thereof in alignment with said urine drainage aperture formed into a central portion of said panel and positioned on, and laterally extendable from, the downwardly facing surface of said panel;

said panel and said conduit being unfolded for use from a substantially flat folded orientation of said panel and a folded orientation of said conduit;

said panel including two inner urine absorbent layers, a thermal layer disposed between the two absorbent layers, and an outer urine impermeable layer said panel having a longitudinal centerline fold line and two spaced apart transverse fold lines for sequentially folding said panel in half along each respective said fold line to achieve compactness of said device.

4. A disposable urine control device as set forth in claim 3, wherein:

said aperture is generally egg-shaped and elongated lengthwise of said panel to facilitate folding along a longitudinal centerline of said panel and said conduit;

said aperture adapted to fit between two fingers of the hand of a user for accurate alignment of said aperture with urine discharge.

5. A disposable urine control device for females during urination in a crouched position comprising:

an elongated flexible flat panel formed of disposable material and having inwardly profiled side margins and enlarged end portions thereof to define a perimeter of said panel;

a perimeter sealing bead formed as a part of said panel and raised upwardly from, and substantially continuously around said perimeter, said perimeter sealing bead providing stiffness and establishing sealing contact around the labia majora;

an inner sealing bead formed as a part of said panel and raised upwardly from and extending between said perimeter and an elongated egg-shaped urine drainage aperture, said inner sealing bead establishing sealing contact around the labia minora to more completely contain urine during urination;

a flexible elongated tubular conduit directly connected in alignment with said urine drainage aperture formed into a central portion of said panel;

said panel and said conduit being positioned for use from a substantially flat folded in half orientation of said panel and said conduit;

said panel including two inner urine absorbent layers, a thermal layer disposed between the two absorbent layers, and an outer urine impermeable layer said panel having a longitudinal centerline fold line and two spaced apart transverse fold lines for sequentially folding said panel in half along each respective said fold line to achieve compactness of said device.

6. A disposable urine control device for females during urination in a crouched position comprising:

an elongated flexible folded flat panel formed of disposable material and having inwardly profiled side margins and enlarged end portions thereof to define a perimeter of said panel;

a perimeter sealing bead formed as a part of said panel and extending upwardly from, and substantially continuously around said perimeter, said perimeter sealing bead providing stiffness and sealing against the labia majora to contain urine within said perimeter sealing bead during urination;

a flexible elongated folded conduit formed into a one-piece unit with said panel and being directly connected in alignment with a urine drainage aperture formed into, and laterally extending from, a central portion of said panel into a tubular configuration to convey urine from an open lower end of said conduit;

said panel and said conduit being unfolded for use from a substantially flat folded orientation of said panel and a folded orientation of said conduit;

said panel including two inner urine absorbent layers, a thermal layer disposed between the two absorbent layers, and an outer urine impermeable layer said panel having a longitudinal centerline fold line and two spaced apart transverse fold lines with said conduit being therebetween wherein said panel is sequentially thrice folded in half about said fold lines while said conduit is folded in half to achieve compactness of said device.

* * * * *